(12) United States Patent
Lin et al.

(10) Patent No.: US 7,893,234 B2
(45) Date of Patent: Feb. 22, 2011

(54) EPSP SYNTHASE HIGHLY TOLERANT OF GLYPHOSATE

(75) Inventors: Min Lin, Beijing (CN); Kexuan Tang, Shanghai (CN); Yiping Wang, Beijing (CN); Jin Wang, Chengdu (CN); Yu Zhu, Madison, WI (US)

(73) Assignee: Si Chuan Heben Biotic Engineering Co. Ltd., Chengdu, Sichuan Province (CN)

( * ) Notice: Subject to any disclaimer, the term of this patent is extended or adjusted under 35 U.S.C. 154(b) by 739 days.

(21) Appl. No.: 11/747,868

(22) Filed: May 11, 2007

(65) Prior Publication Data

US 2009/0312185 A1    Dec. 17, 2009

Related U.S. Application Data

(62) Division of application No. 10/913,651, filed on Aug. 6, 2004, now Pat. No. 7,238,508.

(30) Foreign Application Priority Data

Aug. 8, 2003    (WO)    ............... PCT/CN03/00651

(51) Int. Cl.
    C07H 20/04    (2006.01)
    C12N 9/10    (2006.01)
    C12N 15/63    (2006.01)
    C12N 5/00    (2006.01)
    C12N 1/20    (2006.01)
    C12N 5/02    (2006.01)
    A01H 5/00    (2006.01)

(52) U.S. Cl. ............. 536/23.2; 435/320.1; 435/419; 435/69.1; 435/252.3; 435/325; 435/410; 435/193; 800/300

(58) Field of Classification Search ............. None
    See application file for complete search history.

(56) References Cited

U.S. PATENT DOCUMENTS

| 4,769,061 A | 9/1988 | Comai |
| 4,940,835 A | 7/1990 | Shah et al. |
| 4,971,908 A | 11/1990 | Kishore et al. |
| 5,094,945 A | 3/1992 | Comai |
| 5,145,783 A | 9/1992 | Kishore et al. |
| 5,310,667 A | 5/1994 | Eichholtz et al. |
| 5,633,435 A | 5/1997 | Barry et al. |
| 5,866,775 A | 2/1999 | Eichholtz et al. |
| 7,314,974 B2 * | 1/2008 | Cao et al. ............. 800/289 |

FOREIGN PATENT DOCUMENTS

| EP | 0 293 358 A2 | 5/1988 |
| EP | 0 409 815 A1 | 7/1990 |
| WO | WO 91/04323 | 4/1991 |
| WO | WO 92/06201 | 4/1992 |

* cited by examiner

*Primary Examiner*—Delia M Ramirez
*Assistant Examiner*—Md. Younus Meah
(74) *Attorney, Agent, or Firm*—Hogan Lovells US LLP

(57) ABSTRACT

An isolated polypeptide comprising an amino acid sequence that is at least 62% identical to SEQ ID NO:2. The polypeptide, when present in a cell, increases the cell's ability to tolerate glyphosate. Also disclosed are related nucleic acid, antibody, vector, transgenic plant, as well as uses thereof.

36 Claims, No Drawings

EPSP SYNTHASE HIGHLY TOLERANT OF GLYPHOSATE

RELATED APPLICATION

The present application is a divisional application of U.S. patent application Ser. No. 10/913,651, filed on Aug. 6, 2004, now U.S. Pat. No. 7,238,508, which claims priority to PCT/CN03/00651, filed on Aug. 8, 2003, entitled "EPSP SYNTHASE HIGHLY TOLERANT TO GLYPHOSATE AND ITS CODING SEQUENCE.", The contents of U.S. patent application Ser. No. 10/913,651 and PCT/CN03/00651 are hereby incorporated by reference as if fully set forth herein.

FIELD OF THE INVENTION

The present invention generally relates to 5-enolpyruvylshikimate-3-phosphate (EPSP) synthase. More specifically, the invention relates to an EPSP synthase gene encoding a polypeptide highly tolerant to glyphosate, and products containing the gene.

BACKGROUND OF THE INVENTION

Glyphosate is a non-selective, broad spectrum and post-emergence herbicide. Glyphosate applied to foliage is absorbed by leaves and rapidly moves through the plant. Once absorbed, it prevents the plant from producing essential aromatic amino acids. This reduces the production of protein in the plant, and inhibits plant growth.

EPSP synthase is the sixth enzyme on the shikimate pathway, which is essential for the synthesis of aromatic amino acids. Based on the studies of chemically induced aroA mutants, it has been confirmed that EPSP synthase is encoded by the aroA gene. Recent advances in genetic engineering have made it possible to produce transgenic plants with unique characteristics of agronomic importance. Generation of glyphosate tolerant transgenic plants (e.g., containing glyphosate tolerant EPSP synthase) will reduce the cost for weed control.

SUMMARY OF THE INVENTION

The invention is based on the discovery of a novel EPSP synthase that is highly tolerate to glyphosate. The amino acid sequence (SEQ ID NO:2) of the newly discovered EPSP synthase and its coding nucleic acid sequence (SEQ ID NO:1) are shown below:

```
ctcctacagt tagggcaagt cccccaccac tcgacaagc atg gcg tgt ttg cct      54
                                            Met Ala Cys Leu Pro      5 gat gat tcg ggt ccg cat gtc ggc cac tcc acg cca cct cgc ctt gac    102
Asp Asp Ser Gly Pro His Val Gly His Ser Thr Pro Pro Arg Leu Asp     21 cag gag cct tgt acc ttg agt tcg cag aaa acc gtg acc gtt aca ccg    150
Gln Glu Pro Cys Thr Leu Ser Ser Gln Lys Thr Val Thr Val Thr Pro     37 ccc aac ttc ccc ctc act ggc aag gtc gcg ccc ccc ggc tcc aaa tcc    198
Pro Asn Phe Pro Leu Thr Gly Lys Val Ala Pro Pro Gly Ser Lys Ser     53 att acc aac cgt gcg ctg ttg ctg gcg gca ttg gcc aag ggc acc agc    246
Ile Thr Asn Arg Ala Leu Leu Leu Ala Ala Leu Ala Lys Gly Thr Ser     69 cgt ttg agc ggt gcg ctc aaa agc gat gac acg cgc cac atg tcg gtc    294
Arg Leu Ser Gly Ala Leu lys Ser Asp Asp Thr Arg His Met Ser Val     85 gcc ctg cgg cag atg ggc gtc acc atc gac gag ccg gac gac acc acc    342
Ala Leu Arg Gln Met Gly Val Thr Ile Asp Glu Pro Asp Asp Thr Thr    101 ttt gtg gtc acc agc caa ggc tcg ctg caa ttg ccg gcc cag ccg ttg    390
Phe Val Val Thr Ser Gln Gly Ser Leu Gln Leu Pro Ala Gln Pro Leu    117 ttc ctc ggc aac gct ggc acc gcc atg cgc ttt ctc acg gct gcc gtg    438
Phe Leu Gly Asn Ala Gly Thr Ala Met Arg Phe Leu Thr Ala Ala Val    133 gcc acc gtg caa ggc acc gtg gta ctg gac ggc gac gag tac atg caa    486
Ala Thr Val Gln Gly Thr Val Val Leu Asp Gly Asp Glu Tyr Met Gln    149 aaa cgc ccg att ggc ccg ctg ctg gct acc ctg ggc cag aac ggc atc    534
Lys Arg Pro Ile Gly Pro Leu Leu Ala Thr Leu Gly Gln Asn Gly Ile    165 cag gtc gac agc ccc acc ggt tgc cca ccg gtc acc gtg cac ggc atg    582
Gln Val Asp Ser Pro Thr Gly Cys Pro Pro Val Thr Val His Gly Met    181 ggc aag gtc cag gcc aag cgt ttc gag att gat ggt ggt ttg tcc agc    630
Gly Lys Val Gln Ala Lys Arg Phe Glu Ile Asp Gly Gly Leu Ser Ser    197 cag tac gta tcg gcc ctg ctg atg ctc gcg gcg tgc ggc gaa gcg ccg    678
Gln Tyr Val Ser Ala Leu Leu Met Leu Ala Ala Cys Gly Glu Ala Pro    213 att gaa gtg gcg ctg acc ggc aag gat atc ggt gcc cgt ggc tac gtg    726
Ile Glu Val Ala Leu Thr Gly Lys Asp Ile Gly Ala Arg Gly Tyr Val    229 gac ctg acc ctc gac tgc atg cgt gcc ttc ggg gcc cag gtg gac gcc    774
```

-continued

```
Asp Leu Thr Leu Asp Cys Met Arg Ala Phe Gly Ala Gln Val Asp Ala        245 gtg gac gac acc acc tgg cgc gtc gcc ccc acc ggc tat acc gcc cat        822
Val Asp Asp Thr Thr Trp Arg Val Ala Pro Thr Gly Tyr Thr Ala His        261 gat tac ctg atc gaa ccc gat gcg tcc gcc gcc acg tat ttg tgg gcc        870
Asp Tyr Leu Ile Glu Pro Asp Ala Ser Ala Ala Thr Tyr Leu Trp Ala        277 gca gaa gtg ctg acc ggt ggg cgt atc gac atc ggc gta gcc gcg cag        918
Ala Glu Val Leu Thr Gly Gly Arg Ile Asp Ile Gly Val Ala Ala Gln        293 gac ttc acc cag ccc gac gcc aag gcc cag gcc gtg att gcg cag ttc        966
Asp Phe Thr Gln Pro Asp Ala Lys Ala Gln Ala Val Ile Ala Gln Phe        309 ccg aac atg caa gcc acg gtg gta ggc tcg caa atg cag gat gcg atc       1014
Pro Asn Met Gln Ala Thr Val Val Gly Ser Gln Met Gln Asp Ala Ile        325 ccg acc ctg gcg gtg ctc gcc gcg ttc aac aac acc ccg gtg cgt ttc       1062
Pro Thr Leu Ala Val Leu Ala Ala Phe Asn Asn Thr Pro Val Arg Phe        341 act gaa ctg gcg aac ctg cgc gtc aag gaa tgt gac cgc gtg cag gcg       1110
Thr Glu Leu Ala Asn Leu Arg Val Lys Glu Cys Asp Arg Val Gln Ala        357 ctg cac gat ggc ctc aac gaa att cgc ccg ggc ctg gcg acc atc gag       1158
Leu His Asp Gly Leu Asn Glu Ile Arg Pro Gly Leu Ala Thr Ile Glu        373 ggc gat gac ctg ctg gtc gcc agc gac ccg gcc ctg gca ggc acc gcc       1206
Gly Asp Asp Leu Leu Val Ala Ser Asp Pro Ala Leu Ala Gly Thr Ala        389 tgc acc gca ctg atc gac acc cac gcc gac cat cgc atc gcc atg tgc       1254
Cys Thr Ala Leu Ile Asp Thr His Ala Asp His Arg Ile Ala Met Cys        405 ttt gcc ctg gcc ggg ctt aaa gtc tcg ggc att cgc att caa gac ccg       1302
Phe Ala Leu Ala Gly Leu Lys Val Ser Gly Ile Arg Ile Gln Asp Pro        421 gac tgc gtg gcc aag acc tac cct gac tac tgg aaa gcc tgg ccc agc       1350
Asp Cys Val Ala Lys Thr Tyr Pro Asp Tyr Trp Lys Ala Trp Pro Ser        437 ctg ggc gtt cac cta aac gac tgacacacaa aacctgtagc agagcttgct          1401
Leu Gly Val His Leu Asn Asp (SEQ ID NO: 2)                             444 cgcgaaaaac gcacacgtgc cgcgtttgtt caggaaacac gcgttatcgt tgacgtttat     1461
cgagctaagc tcgctcctac attttgcagc gagatcttg (SEQ ID NO: 1)             1500
```

The open reading frame ("ORF;" SEQ ID NO:3) includes bp 40 to 1371 of SEQ ID NO:1.

Accordingly, the invention features an isolated polypeptide including an amino acid sequence that is at least 62% (i.e., any number between 62% and 100%, e.g., 65, 70, 75, 80, 85, 90, 95, 99 or 100%) identical to SEQ ID NO:2. When present in a cell, the polypeptide increases the cell's ability to tolerate glyphosate. The polypeptide of the invention can be used for producing an antibody (either monoclonal or polyclonal) that selectively binds to the polypeptide. The antibody in turn is useful for detecting the presence of the polypeptide in vivo and in vitro. For example, such an antibody can be used to verify the expression of the polypeptide in a transgenic plant.

An "isolated polypeptide" refers to a polypeptide substantially free from naturally associated molecules, i.e., it is at least 10% (i.e., any number between 10% and 100%) pure by dry weight. Purity can be measured by any appropriate standard method, for example, by column chromatography, polyacrylamide gel electrophoresis, or HPLC analysis.

The "percent identity" of two amino acid sequences is determined using the algorithm of Karlin and Altschul ((1990) Proc. Natl. Acad. Sci. USA 87:2264-2268), modified as in Karlin and Altschul ((1993) Proc. Natl. Acad. Sci. USA 90; 5873-5877). Such an algorithm is incorporated into the XBLAST programs of Altschul et al. ((1990) J. Mol. Biol. 215:403-410). BLAST protein searches are performed with the XBLAST program, score=50, wordlength=3. Where gaps exist between two sequences, Gapped BLAST is utilized as described in Altschul et al. ((1997) Nucleic Acids Res. 25:3389-3402). When utilizing BLAST and Gapped BLAST programs, the default parameters of the respective programs (e.g., XBLAST) are used. See www.ncbi.nlm.nih.gov.

The invention further features an isolated nucleic acid characterized in that it hybridizes under stringent conditions to SEQ ID NO:1 or 3, or a complementary sequence thereof, as well as a cell (e.g., in a culture or in a transgenic plant) containing a nucleic acid of the invention. Such a nucleic acid can be at least 15 (e.g., at least 30, 50, 100, 200, 500 or 1000) nucleotides in length. An example of a nucleic acid within the invention is an isolated nucleic acid (e.g., a vector) encoding a polypeptide of the invention, e.g., a nucleic acid that contains SEQ ID NO:1 or 3, where the coding sequence is operably linked to an expression control sequence. The nucleic acid and the cell can be used for producing a polypeptide of the invention or generating a transgenic plant. For example, the nucleic acid of the invention can be used to determine whether an EPSP synthase mRNA is expressed in a cell or tissue. The nucleic acid can also be used as a primer in PCR-based detection methods, or as a labeled probe in nucleic acid blots (e.g., Northern and Southern blots).

A plant cell of this invention can be cultivated to generate a transgenic plant. Such a transgenic plant is within the scope of the invention. More specifically, the invention features a transgenic plant comprising an isolated nucleic acid encoding a polypeptide of the invention that is operably linked to an expression control sequence. Expression of the polypeptide allows the plant to become more tolerant to glyphosate. Examples of such transgenic plants include transgenic soybean, cotton, alfalfa, canola, flax, tomato, sugar beet, sunflower, potato, tobacco, corn, wheat, rice, lettuce and rape.

An "isolated nucleic acid" is a nucleic acid removed from its natural environment and thus altered "by the hand of man" from its natural state. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

By hybridization under "stringent conditions" is meant (1) hybridization and wash under low ionic strength and high temperature, e.g., in 0.2×SSC and 0.1% SDS at 60° C.; (2) hybridization in the presence of a denaturing agent, e.g., 50% v/v formamide and 0.1% calf serum/0.1% Ficoll at 42° C.; or (3) hybridization between two strands that are at least 90%, and preferably at least 95%, identical.

The term "operably linked" refers to functional linkage between an expression control sequence and a nucleic acid sequence. The operably linked expression control sequence regulates transcription of the nucleic acid sequence. Examples of an "expression control sequence" includes a promoter, a transcription termination signal, an enhancer, a silencer, an insulator, and the like.

In addition, the invention features a method of producing a polypeptide by cultivating a cell containing a nucleic acid encoding a polypeptide of the invention such that the polypeptide is expressed in the cell. Conditions for polypeptide expression are well known in the art. See, e.g., Sambrook et al. (1989) Molecular Cloning: A Laboratory Manual, 2nd ed., Cold Spring Harbor Laboratory, Cold Spring Harbor Laboratory Press, Cold Spring Harbor, N.Y.

The invention also provides a method of increasing a plant's ability to tolerate glyphosate. The method involves introducing a vector of the invention into a plant cell, cultivating the plant cell, and regenerating a transgenic plant from the cell. A transgenic plant thus produced has increased tolerance to glyphosate compared to a wild-type plant.

Plants with increased glyphosate tolerance risk less damages when exposed to the herbicide. Consequently, the invention features a method of selectively controlling weeds in a field. The method includes growing a transgenic plant of the invention in a field and applying to the field a sufficient amount of glyphosate. A "sufficient amount" refers to the quantity of the herbicide that enables control of the weeds, yet in the meantime, does not significantly affect the plant, e.g., in quality and yield.

The above-mentioned and other features of this invention and the manner of obtaining and using them will become more apparent, and will be best understood, by reference to the following description.

DETAILED DESCRIPTION OF THE INVENTION

The invention relates to a novel EPSP synthase. Unexpectedly, this enzyme has been found to be highly resistant to glyphosate. For example, bacteria transformed with DNA encoding this enzyme grew in media containing 10-150 mM glyphosate, and a transgenic tobacco grew in the presence of 15 mM glycosate (see Examples 1 and 5 below).

At the amino acid sequence level, SEQ ID NO:2 has a low homology to known Class I EPSP synthases (from bacteria such as E. coli and Salmonella typhimurium). For example, the homology between SEQ ID NO:2 and the E. coli EPSP synthase is 30.4%, and the homology between SEQ ID NO:2 and the Salmonella typhimurium EPSP synthase is 31.7%. SEQ ID NO:2 shows 24.53% homology to Agrobacterial CP4 EPSP synthase disclosed in Monsanto's patents. Moreover, SEQ ID NO:2 does not contain the L-G-N-A-A-T-A (SEQ ID NO:4) sequence at positions corresponding to the a.a. 80-120 region disclosed in Monsanto's patents (e.g., U.S. Pat. No. 4,971,908). It also differs from the A-L-L-M-X1-A-P-L-T (SEQ ID NO:5) sequence at positions corresponding to the a.a. 170-210 region disclosed in Monsanto's patents (e.g., U.S. Pat. No. 5,866,775), wherein X1 is alanine, serine or threonine. For example, SEQ ID NO:2 is only 36.6% homologous to a petunia EPSP synthase in the a.a. 170-210 region. Comparison with all known EPSP synthases revealed that SEQ ID NO: 2 has the highest (60.7%) similarity to that of EPSP synthase from Agrobacterium tumefaciens C58 and is 20.53% similar to that of EPSP synthase from Pseudonomas mallei of the same genus.

Polypeptides

One object of the invention is to provide an isolated polypeptide comprising an amino acid sequence that is at least 62% (i.e., any number between 62% and 100%, e.g., 65, 70, 75, 80, 85, 90, 95, 99 or 100%) identical to SEQ ID NO:2. A cell expressing this polypeptide becomes more tolerant to glyphosate (e.g., 10, 20, 30, 40, 50, 60, 70, 80, 90, 100, 110, 120, 130, 140, 150 mM glyphosate). Such a polypeptide may be a fragment, e.g., a biologically active portion of SEQ ID NO:2, for use as an immunogen or antigen to raise or test (or more generally to bind) an anti-EPSP synthase antibody. In a preferred embodiment, the polypeptide of the invention has an amino acid sequence shown in SEQ ID NO:2. The polypeptide of the invention can be isolated from cells (e.g., bacterial cells transformed with a nucleic acid encoding SEQ ID NO:2 as described Examples 1 and 4) or tissue sources (e.g., tissues from transgenic plants as described in the Example 5) using standard protein purification techniques. It can also be produced by recombinant DNA techniques or synthesized chemically.

Other embodiments include a polypeptide that contains one or more changes in amino acid sequence, e.g., a change in an amino acid residue which is not essential for EPSP synthase's ability to tolerate glyphosate. Such a polypeptide differs in amino acid sequence from SEQ ID NO:2, yet retains its biological activity. In some embodiments, the difference is a conservative substitution, while in others, the difference is a non-conservative substitution. Like point mutations, insertion and deletion mutants can be generated by mutagenesis according to the procedures well known in the art.

The term "conservative substitution," as used herein, denotes the replacement of an amino acid by another biologically similar residue. Examples of conservative substitutions include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like.

The amino acid sequences and structures of EPSP synthases from various species have been well studies. See, e.g., Park et al. (2004) Molecular Microbiology 51(4):963-971; Eschenburg et al. (2002) Planta 216:129-135; Schonbrunn et al. (2001) PNAS 98 (4):1376-1380; U.S. Pat. Nos. 4,769,061;

4,940,835; 4,971,90; 5,094,945; 5,310,667; 5,633,435; 5,866,775; 5,145,783; EP 0293358 A2; EP 0409815 A1; WO 91/04323; and WO 92/06201.

Comparing with the previously known sequences for EPSP synthases, in some embodiments, a polypeptide of the invention does not contain some of the sequence characteristics described in the above-mentioned patents. For example, in one embodiment, the polypeptide does not contain a sequence of L-G-N-A-A-T-A (SEQ ID NO:4) at positions corresponding to a.a. 119-125 of SEQ ID NO:2.

In another embodiment, the polypeptide does not contain a sequence of E-R-P-I-X2-X3-L-V-X4-X5-X6-X7-X8-X9-A (SEQ ID NO:6) at positions corresponding to a.a. 150-164 of SEQ ID NO:2, in wherein X2-5 and X7-8 are any amino acid residues, X6 is either arginine or lysine, and X9 is either aspartic acid or asparagines.

In another embodiment, the polypeptide does not contain a sequence of R-X 10-H-X11-E (SEQ ID NO:7), in which X10 is G, S, T, C, Y, N, Q, D or E; X11 is S or T.

In another embodiment, the polypeptide does not contain a sequence of G-D-K-X12 (SEQ ID NO:8), in which X12 is S or T.

In another embodiment, the polypeptide does not contain a sequence of S-A-Q-X13-K (SEQ ID NO:9), in which X13 is A, R, N, D, C, Q, E, G, H, I, L, K, M, F, P, S, T, W, Y or V.

In another embodiment, the polypeptide does not contain a sequence of N-X14-T-R (SEQ ID NO: 10), in which X14 is A, R, N, D, C, Q, E, G, H, I, L, K, M, F, P, S, T, W, Y or V.

In still another embodiment, the polypeptide does not contain a sequence of A-L-L-M-X15-A-P-L-T (SEQ ID NO:11) at positions corresponding to a.a. 202-210 of SEQ ID NO:2, wherein X15 is either alanine, serine or threonine; or it differs by at least 64% (i.e., any number between 64% and 100%) from other EPSP synthases in this region.

In some embodiments, a polypeptide of the invention contains some sequence characteristics that haven't been found in any other EPSP synthases. For example, in one embodiment, the polypeptide contains a sequence of GKV APPGSKSITNRALLLAALAKGTSRLSGAL (SEQ ID NO:12) at positions corresponding to a.a. 44-75 of SEQ ID NO:2.

In another embodiment, the polypeptide contains a sequence of LFLGNAGTAMRFLTAAVAT (SEQ ID NO:13) at positions corresponding to a.a. 117-135 of SEQ ID NO:2.

In another embodiment, the polypeptide contains a sequence of VLDGDEYMQKRPIGPLLATLGQNGIQV (SEQ ID NO:14) at positions corresponding to a.a. 141-167 of SEQ ID NO:2.

In another embodiment, the polypeptide contains a sequence of LAVLAAFNNTPVRFTELANLRVKECDR VQALHDGLNEIRPGLATIEGDDLL (SEQ ID NO:15) at positions corresponding to a.a. 328-378 of SEQ ID NO:2.

In another embodiment, the polypeptide contains a sequence of IDTHADHRIAMCFALAGL (SEQ ID NO:16) at positions corresponding to a.a. 394-411 of SEQ ID NO:2.

In yet another embodiment, the polypeptide contains a sequence of LTGKDIGARGYVDLTLDC (SEQ ID NO:17) at positions corresponding to a.a. 218-235 of SEQ ID NO:2.

In some embodiments, one or more of the underlined amino acids in SEQ ID NOs:12-17 are reserved while other amino acids may be changed.

Furthermore, comparison of SEQ ID NO:2 with *E. coli* and petunia EPSP synthases revealed some conserved amino acid residues (underlined below). In some embodiments, a polypeptide of the invention contains one or more of these residues (i.e., R151. S196, S197, Q198, D323, N346, K350, R354, R401, and K426 of SEQ ID NO:2).

```
                                191              213
E. coli EPSP synthase (112)    DIVLTGEPRMKERPIGHLVDALR  (SEQ ID NO: 18)
SEQ ID NO: 2          (139)    TVVLDGDEYMQKRPIGPLLATLG  (SEQ ID NO: 19)
Petunia EPSP synthase (191)    RYVLDGVPRMRERPISDLVDGLK  (SEQ ID NO: 20)
Consensus             (191)     IVLDGDPRMKERPIG LVDALK  (SEQ ID NO: 21)

244       259
E. coli EPSP synthase (163)    DVDGSVSSQFLTALLM  (SEQ ID NO: 22)
SEQ ID NO: 2          (190)    EIDGGLSSQYVSALLM  (SEQ ID NO: 23)
Petunia EPSP synthase (244)    KLSGSISSQYLTALLM  (SEQ ID NO: 24)
Consensus             (244)    DIDGSISSQYLTALLM  (SEQ ID NO: 25)

400      413
E. coli EPSP synthase (309)    NHIPDAAMTIATAA   (SEQ ID NO: 26)
SEQ ID NO: 2          (320)    -QMQDAIPTLAVLA   (SEQ ID NO: 27)
Petunia EPSP synthase (399)    NKMPDVAMTLAVVA   (SEQ ID NO: 28)
Consensus             (400)    N MPDAAMTLAVLA   (SEQ ID NO: 29)

425      439
E. coli EPSP synthase (334)    IYNWRVKETDRLFAM  (SEQ ID NO: 30)
SEQ ID NO: 2          (344)    LANLRVKECDRVQAL  (SEQ ID NO: 31)
Petunia EPSP synthase (424)    VASWRVKETERMIAI  (SEQ ID NO: 32)
Consensus             (425)    IANWRVKETDRL AI  (SEQ ID NO: 33)

477       489
E. coli EPSP synthase (381)    TYNDHRMAMCFSL    (SEQ ID NO: 34)
SEQ ID NO: 2          (396)    THADHRIAMCFAL    (SEQ ID NO: 35)
Petunia EPSP synthase (471)    TYDDHRMAMAFSL    (SEQ ID NO: 36)
Consensus             (477)    TY DHRMAMCFSL    (SEQ ID NO: 37)

503      514
E. coli EPSP synthase (407)    KCTAKTFPDYFE     (SEQ ID NO: 38)
SEQ ID NO: 2          (422)    DCVAKTYPDYWK     (SEQ ID NO: 39)
Petunia EPSP synthase (497)    GCTRKTFPNYFD     (SEQ ID NO: 40)
Consensus             (503)     CTAKTFPDYFD     (SEQ ID NO: 41)
```

Two or more of the individual embodiments described above may be combined.

In another aspect, the invention provides chimeric or fusion proteins containing the polypeptide of the invention. As used herein, a "chimeric protein" or "fusion protein" includes a polypeptide of the invention linked to a foreign polypeptide. A "foreign polypeptide" is not substantially homologous to a polypeptide of the invention. The foreign polypeptide can be fused to the N-terminus or C-terminus of the polypeptide of the invention.

The fusion protein can include a moiety which has a high affinity for a ligand. For example, the fusion protein can be a GST fusion protein in which a polypeptide of the invention is fused to the C-terminus of GST. Such fusion proteins can facilitate the purification of the polypeptide. Alternatively, the fusion protein can contain a heterologous signal sequence at its N-terminus. In certain host cells, expression, secretion or transport of a protein can be increased through use of a heterologous signal sequence. For example, in a plant cell, a polypeptide of the invention may be fused with a chloroplast transit peptide. The chloroplast transit peptide allows the polypeptide to be transported from the cytoplasm of the plant cell into the chloroplast, thereby conferring a substantial degree of glyphosate resistance. Expression vectors are commercially available that already encode a fusion moiety (e.g., a GST polypeptide). A nucleic acid encoding a polypeptide of the invention can be cloned into such an expression vector so that the fusion moiety is linked in-frame to the polypeptide.

Antibodies

In another aspect, the invention provides an antibody against the polypeptide of the invention, or a fragment thereof (e.g., an antigen-binding fragment thereof). The term "antibody," as used herein, refers to an immunoglobulin molecule or immunologically active portion thereof, i.e., an antigen-binding portion. It comprises at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, e.g., Kabat et al. (1991) Sequences of Proteins of Immunological Interest, Fifth Edition, U.S. Department of Health and Human Services, NIH Publication No. 91-3242, and Chothia et al. (1987) J. Mol. Biol. 196:901-917). Each VH and VL is composed of three CDR's and four FRs, arranged from amino-terminus to carboxy-terminus in the following order: FR1, CDR1, FR2, CDR2, FR3, CDR3, FR4.

An antibody of the invention can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and fight chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. Full-length immunoglobulin "light chains" (about 25 KDa or 214 amino acids) are encoded by a variable region gene at the N-terminus (about 110 amino acids) and a kappa or lambda constant region gene at the C-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion" or "fragment"), as used herein, refers to one or more fragments of a full-length antibody that retain the ability to specifically bind to the antigen, i.e., a polypeptide of the invention. Examples of antigen-binding fragments of the antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426, and Huston et al. (1988) Proc. Natl. Acad. Sci. USA 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

An antibody of the invention can be a polyclonal or a monoclonal antibody. In other embodiments, the antibody can be recombinantly produced, e.g., produced by phage display or by combinatorial methods. Phage display and combinatorial methods for generating antibodies are known in the art (as described in, e.g., U.S. Pat. Nos. 6,756,196; 5,223,409; WO 92/18619; WO 91/17271; WO 92/20791; WO 92/15679; WO 93/01288; WO 92/01047; WO 92/09690; WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffhs et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982).

In preferred embodiments, an antibody can be made by immunizing with a purified antigen, crude tissue preparation, whole cell, lysed cell, or cell fraction.

A full-length polypeptide of the invention or an antigenic peptide fragment of it can be used as an immunogen or can be used to identify antibodies made with other immunogens, e.g., cells, and the like. The antigenic peptide should include at least 8 amino acid residues of the amino acid sequence shown in SEQ ID NO:2 and encompasses an epitope. Preferably, the antigenic peptide includes at least 10 amino acid residues, more preferably at least 15 amino acid residues, even more preferably at least 20 amino acid residues, and most preferably at least 30 amino acid residues.

Antibodies which bind only the native form of the polypeptide of the invention, only the denatured or otherwise non-native form, or which bind both, are with in the invention. Antibodies with linear or conformational epitopes are within the invention. Conformational epitopes can sometimes be identified by identifying antibodies which bind to native but not denatured form of the polypeptide.

Preferred epitopes encompassed by the antigenic peptide are regions located on the surface of the polypeptide, e.g., hydrophilic regions, as well as regions with high antigenicity. For example, an Emini surface probability analysis of the polypeptide sequence can be used to indicate the regions that have a particularly high probability of being localized to the surface of the polypeptide and are thus likely to constitute surface residues useful for targeting antibody production.

In preferred embodiments, antibodies can bind one or more of purified antigens, tissues, e.g., tissue sections, whole cells, lysed cells, and cell fractions.

The antibody can be a single chain antibody. A single-chain antibody (scFV) may be engineered (see, for example, Colcher et al. (1999) Ann N Y Acad Sci 880:263-80 and Reiter (1996) Clin Cancer Res 2:245-52). The single chain antibody can be dimerized or multimerized to generate multivalent antibodies having specificities for different epitopes of the same target.

An antibody (e.g., monoclonal antibody) can be used to isolate a polypeptide of the invention by standard techniques, such as affinity chromatography or immunoprecipitation. Moreover, an antibody can be used to detect the polypeptide (e.g., in a cellular lysate or cell supernatant) in order to evaluate the abundance and pattern of expression of the polypeptide. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; examples of luminescent materials include luminol; examples of bioluminescent materials include luciferase, luciferin and aequorin, and examples of suitable radioactive materials include $^{125}I$, $^{131}I$, $^{35}S$ or $^{3}H$.

The invention also includes a nucleic acid which encodes an antibody of the invention. Also included are a vector containing the nucleic acid and a cell transformed with the vector, particularly a cell which is useful for producing an antibody. The invention also includes a method of using a cell, e.g., a hybridoma, to make an antibody of the invention.

Nucleic Acids

In yet another aspect, the invention provides an isolated nucleic acid that encodes a polypeptide of the invention. Also included is a nucleic acid fragment suitable for use as a hybridization probe, which can be used, e.g., to identify a nucleic acid (a DNA or mRNA) encoding a polypeptide of the invention, and a fragment suitable for use as a primer, e.g., a PCR primer for amplification or mutation of the nucleic acid.

In one embodiment, an isolated nucleic acid of the invention includes the nucleotide sequence shown in SEQ ID NO:1 or a portion thereof. For example, the nucleic acid may include the coding region of SEQ ID NO:1, as shown in SEQ ID NO:3. In another embodiment, the isolated nucleic acid of the invention includes a nucleic acid molecule which is a complement of the nucleotide sequence shown in SEQ ID NO:1 or 3, or a portion thereof. In other embodiments, the nucleic acid of the invention is sufficiently complementary to the nucleotide sequence shown in SEQ ID NO:1 or 3, such that it can hybridize (e.g., under stringency conditions described above) to the nucleotide sequence shown in SEQ ID NO:1 or 3, thereby forming a stable duplex.

A nucleic acid of the invention can include only a portion of the nucleic acid sequence of SEQ ID NO:1 or 3. For example, such a nucleic acid can include a fragment which can be used as a probe or primer or a fragment encoding a portion of a polypeptide of the invention, e.g., an immunogenic or biologically active portion of the polypeptide. The nucleotide sequence determined from the cloning of the new EPSP synthase gene allows for the generation of probes and primers designed for use in identifying or cloning other EPSP synthases, or fragments thereof, as well as EPSP synthase homologues, or fragments thereof, from other species.

Typically a probe/primer is an isolated or purified oligonucleotide. The oligonucleotide typically includes a region of nucleotide sequence that hybridizes under stringency conditions described above to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or 3, or of a naturally occurring allelic variant or mutant of SEQ ID NO:1 or 3. Preferably, a primer is less than about 200, 150, 120, 100, 50, 30, 20 or 10 nucleotides in length. A probe may be 10, 20, 30, 50, 100, 200, 300, 400, 500, 600, 700, 800, 900, 1000 or more nucleotides in length. In one embodiment, the probe or primer is attached to a solid support, e.g., in a microarray analysis.

The invention further encompasses nucleic acids that differ from the nucleotide sequence shown in SEQ ID NO:1 or 3. Such differences can be due to degeneracy of the genetic code (and result in a nucleic acid which encodes the same polypeptide). In another embodiment, an isolated nucleic acid of the invention has a nucleotide sequence encoding a polypeptide having an amino acid sequence which differs, by at least 1, but less than 5, 10, 20, 50, 100 or 150 amino acid residues that shown in SEQ ID NO:2. If alignment is needed for this comparison, the sequences should be aligned for maximum homology. "Looped" out sequences from deletions or insertions, or mismatches, are considered differences.

In one embodiment, a nucleic acid includes a nucleotide sequence that includes part, or all, of the coding region and extends into either (or both) the 5' or 3' non-coding region.

Nucleic acids of the inventor can be chosen for having codons, which are preferred, or non-preferred, for a particular expression system. For example, the nucleic acid can be one in which at least one codon, and preferably at least 10% or 20% of the codons, has been altered such that the sequence is optimized for expression e.g, in bacterial or plant cells.

Variants of the nucleic acid of the invention can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions described above.

Allelic variants include both functional and non-functional proteins. Functional allelic variants are naturally occurring amino acid sequence variants within a population that maintain the EPSP synthase activity. Functional allelic variants will typically contain only conservative substitution of one or more amino acids of SEQ ID NO:2, or substitution, deletion or insertion of non-critical residues in non-critical regions of the polypeptide. Non-functional allelic variants are naturally-occurring amino acid sequence variants that do not have the EPSP synthase activity. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Vectors and Cultured Cells

An additional aspect of the invention includes vectors containing a nucleic acid encoding a polypeptide of the invention. Examples of such vectors are described in Examples 1 and 4 below. As used herein, the term "vector" refers to a nucleic acid molecule capable of transporting another nucleic acid to which it has been linked and can include a plasmid or cosmid vector. The vector can be capable of autonomous replication or it can integrate into a host DNA.

A vector can include a nucleic acid of the invention in a form suitable for expression of the nucleic acid in a host cell. Preferably the recombinant expression vector includes one or more expression control sequences operatively linked to the nucleic acid sequence to be expressed. Expression control sequences include those which direct constitutive expression of a nucleotide sequence, as well as tissue-specific regulatory and/or inducible sequences. The design of the expression vector can depend on such factors as the choice of the host cell to be transformed, the level of expression of polypeptide desired, and the like. The expression vectors of the invention can be introduced into host cells to thereby produce the polypeptide, as well as a fusion polypeptide, a mutant form of the polypeptide, and the like.

The recombinant expression vectors of the invention can be designed for expression of the polypeptide of the invention in prokaryotic or eukaryotic cells. For example, polypeptides of the invention can be expressed in E. coli or plant cells. Suitable host cells are discussed further in Goeddel (1990) Gene Expression Technology, Methods in Enzymology 185, Academic Press, San Diego, Calif. Alternatively, the recombinant expression vector can be transcribed and translated in vitro, for example, using T7 promoter regulatory sequences and T7 polymerase.

Expression of polypeptides in prokaryotes is most often carried out in E. coli with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (1) to increase expression of a recombinant polypeptide; (2) to increase the solubility of the recombinant polypeptide; and (3) to aid in the purification of the recombinant polypeptide by acting as a ligand in affinity purification. Often, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech, Inc.; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide. Purified fusion polypeptides can be used in EPSP synthase activity assays or to generate antibodies.

To maximize recombinant polypeptide expression in E. coli, the polypeptide is usually expressed in a host bacteria with an impaired capacity to proteolytically cleave the recombinant polypeptide (Gottesman (1990) Gene Expression Technology, Methods in Enzymology 185, Academic Press, San Diego, Calif., p 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the promoter is an inducible promoter, e.g., a promoter regulated by a heterologous polypeptide (e.g., the tetracycline-inducible systems, "Tet-On" and "Tet-Off"; see, e.g., Clontech Inc., CA, Gossen and Bujard (1992) Proc. Natl. Acad. Sci. USA 89:5547).

When used in plant cells, promoters which are known or found to cause transcription of EPSP synthase genes in plant cells can be used (see, e.g., U.S. Pat. No. 4,940,835). Such promoters may be obtained from plants or viruses and include, but are not limited to, the 35S and 19S promoters of cauliflower mosaic virus and promoters isolated from plant genes such as EPSP synthases and ssRUBISCO genes, and promoters obtained from T-DNA genes of Agrobacterium tumefaciens such as nopaline and mannopine synthases genes.

These promoters may be further modified if desired to alter their expression characteristics. For example, the CaMV 35S promoter may be ligated to the portion of the ssRUBISCO gene which represses the expression of ssRUBISCO in the absence of light, to create a promoter which is active in leaves but not in roots. The RNA produced from the EPSP synthase gene may contain a 5 non-translated leader sequence. This sequence may be derived from any gene and may be specifically modified so as to increase translation of the mRNA. The 5' non-translated regions may be derived from viral RNAs, other suitable eukaryotic genes or a synthetic gene sequence. It may be part of the 5' end of the non-translated region of the coding sequence for the EPSP synthase polypeptide or derived from an unrelated promoter or coding sequence.

In one embodiment. a polypeptide of the invention is fused to a chloroplast transit peptide (CTP). After the fusion polypeptide is produced in the cytoplasm of a transformed plant cell, the CTP leader sequence causes the polypeptide to be imported into chloroplasts, and the CTP leader sequence is removed from the remainder of the polypeptide so that an active portion of the polypeptide exists and functions inside the chloroplast. Suitable CTP's may be obtained from various sources. Most preferably, the CTP is obtained from the endogenous EPSP synthase gene of the subject plant to be transformed. Alternately, a CTP from an EPSP synthase gene of another plant or a CTP from another plant gene may be used. Suitable CTP sequences can be determined, e.g., by assaying the chloroplast uptake of the polypeptide comprising the CTP of interest as described in U.S. Pat. No. 4,940, 835.

The 3' non-translated region may contain a polyadenylation signal which functions in plants to cause the addition of polyadenylate nucleotides to the 3' end of the mRNA. The 3' non-translated region naturally associated with a plant EPSP synthase gene may be used. Examples of other suitable 3' regions are the 3' transcribed, non-translated regions containing the polyadenylation signal of the nopaline synthase (NOS) gene of the *Agrobacterium* tumor-inducing (Ti) plasmid or the conglycinin (7S) storage protein gene.

Another aspect the invention provides a cultured cell which includes a nucleic acid of the invention, e.g., within a recombinant expression vector which allows it to homologously recombine into a specific site of the host cell's genome. A host cell can be any prokaryotic or eukaryotic cell. For example, a polypeptide of the invention can be expressed in a bacterial cell or a plant cell. Other suitable host cells are known to those skilled in the art.

Vector DNA can be introduced into host cells via conventional transformation or transfection techniques, including calcium phosphate or calcium chloride co-precipitation, DEAE-dextran-mediated transfection, lipofection, or electroporation.

Transgenic Plants

A nucleic acid encoding a polypeptide of the invention is inserted into the genome of a plant by any suitable method known in the art. Suitable plants include, but are not limited to, soybean, cotton, alfalfa, canola, flax, tomato, sugar beet, sunflower, potato, tobacco, corn, wheat, rice, lettuce and rape.

Suitable plant transformation vectors include those derived from a Ti plasmid of *Agrobacterium tumefaciens* as well as those described in, e.g. Herrera-Estrella et al. (1983) Nature 303:209, Bevan et al. (1983) Nature 304:184, and EPO publication 120,516). In addition to plant transformation vectors derived from the Ti or rootinducing (Ri) plasmids of *Agrobacterium*, alternative methods can be used to insert the nucleic acid into plant cells. Such methods may involve, for example, liposomes, electroporation, chemicals which increase free DNA uptake, and the use of viruses or pollen as vectors. If desired, more than one copy of the nucleic acid may be inserted into the chromosomes of a plant, by methods such as repeating the transformation and selection cycle more than once.

Transformed plant cells can be regenerated into differentiated plants using standard nutrient media supplemented with selected shoot-inducing or root-inducing hormones, using methods described in WO 084/02920 or other methods known to those skilled in the art. For example, glyphosate tolerant transgenic tobacco can be generated using the materials and methods described in Examples 3-5 below.

Uses

A cultured cell or transgenic plant of the invention can be used to produce (i.e., express) a polypeptide of the invention. Accordingly, the invention further provides a method for producing a polypeptide of the invention using a cultured cell or transgenic plant described above. In one embodiment, the method includes culturing the cell or transgenic plant (into which a recombinant expression vector encoding a polypeptide of the invention has been introduced) in a suitable medium such that the polypeptide is produced. In another embodiment, the method further includes isolating the polypeptide from the medium, the cultured cell or the transgenic plant.

A nucleic acid encoding a polypeptide of the invention fused to a CTP sequence also provides a useful selectable marker for plant cell transformation, when transformed and untransformed cells are contacted with appropriate concentrations of glyphosate (which can be routinely determined for any type of plant). The conferrable trait of glyphosate resistance may be particularly useful with certain types of plants (such as alfalfa, soybean and other legumes) which do not exhibit clear selectability using other selectable marker genes (such as kanamycin, methotrexate or hygromycin resistance genes).

In another aspect, the invention provides a method for improving the ability of a plant (e.g., a crop) to tolerate glyphosate by introducing a nucleic acid encoding a polypeptide of the invention (e.g., a vector of the invention) into a plant cell. The transformed cell is cultivated and used to generate a transgenic plant. Expression of the polypeptide in the plant confers higher glyphosate tolerance to the plant.

In yet another aspect, the invention provides a method for selectively controlling weeds in a field where a transgenic plant (e.g., a crop) of the invention is grown. As the transgenic plant is more tolerant to glyphosate, the herbicide may be applied to the field in an amount sufficient to selectively kill or control weeds that may also be growing in the field that are not glyphosate tolerant. This allows the desired glyphosate tolerant plant to take full advantage of the available nutrients in the field for an improved quality and yield.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

Cloning of High Glyphosate Tolerance DNA Fragment

1. Sample Collection from Soil Highly Contaminated with Glyphosate

There are many different bacterial strains which are highly tolerant to glyphosate or other herbicides in the natural environment, especially in those soils sprayed with glyphosate for a long time. Samples were collected from the soil in the open packaging area in Hebei Qifeng Chemical Industrial Co., Ltd. The soil was contaminated with about 50% glyphosate for more than 10 years.

2. Isolation of Total DNA at the Community Level from Soil Highly Contaminated with Glyphosate Using Non-Bacterial-Culture Method Two grams of soil was added into 0.6 g of small beads (diameter<0.11 mm), and vortexed at 4000 rpm twice. The mixture was suspended in 300 µl lysis buffer containing 2% v/v SDS, 12% v/v equilibrated phenol-Tris.HCl (pH 8.0) on ice for one hour. An equal volume (about 700 µl) of equilibrated phenol-Tris.HCl (pH 8.0) buffer was added. The sample was mixed well, followed by centrifuge at 13000 rpm for 5 minutes. The supernatant was mixed with 0.1× volume of 3 M NaAc (pH 5.2), and subsequently 0.6× volume of iso-propylacohol to precipitate DNA. The DNA pellet (crude DNA) was dissolved in 200 µl 1×TE buffer. 100 mg CsCl was weighed and added into a new 1.5 ml Enppendorf tube, and gently mixed with 100 µl crude DNA. The sample was incubated in the dark for 1-3 hours to allow CsCl to dissolve, and then centrifuged at 13000 rpm for 20 minutes at room temperature. 400 µl sterile de-ionized water and 300 µl iso-propylacohol were added to the supernatant, and the mixture was incubated at room temperature for 30 minutes. The solution was centrifuged at 13000 rpm for 20 minutes at room temperature. The supernatant was drained off. The pellet was dissolved in 100 µl 1×TE and 40 µl 8 M KAc, and incubated for 15 minutes at room temperature. The solution was centrifuged at 13000 rpm for 15 minutes at 4° C. The supernatant was mixed with 0.6× volume of iso-propylacohol, incubated for 30 minutes, and centrifuged at 15000 rpm for 20 minutes at room temperature. The DNA pellet was dissolved in 100 µl 1×TE buffer. The Wizard spin column clean-up kit was used to purify DNA samples. The purified DNA was dissolved in 10 mM TE (Tris-EDTA, pH 8.0) to an end volume of 100 µl.

3. Construction of Community Genomic DNA Cosmid Library

A SuperCos1 Cosmid Vector kit (Stratagene Co., Ltd) was used to construct a community genomic DNA cosmid library. The community genomic DNA was digested with restriction endonuclease Sau3AI at 0.006 unit/microgram purified DNA. DNA fragments of about 40 kb were collected using the freeze-thaw method, and then ligated with SuperCos1/BamH1 vector. A cosmid genomic DNA library was constructed according to the manual of Stratagene Co., Ltd. For screening of glyphosate tolerant clones, JM109 E. coli was used as the acceptor bacterium for the genomic library construct, as glyphosate is only effective on an inhibitory medium such as M9 and MOPS. The ligated DNA was packaged into lambda phage particles (Stratagene, Gigapack Gold) according to the manufacturer's protocol. E. coli strain JM109 was infected with the packaged product. The transformants were selected on tetracycline LB media. Positive clones were then plated on LB media containing tetracycline and tetracycline+kanamycin, respectively. Clones growing on both media were considered as negative recombinants resulting from vector ligated with vector DNA. The number of positive transformants was calculated as the total number of colonies minus background false negative colonies. This number was used to determine the titer of the genomic library, which was $4 \times 10^6$ pfu/ml, meeting the requirement for library construction ($>10^6$ pfu/ml).

4. Screening of Glyphosate Tolerant Transformants

The transformants were plated on MOPS LB media containing phosphorus salt and 10 mM glyphosate. About ten clones grew up two days following inoculation. These clones were replicated onto MOPS LB media containing phosphorus salt and different concentrations of glyphosate. The transformant with highest glyphosate tolerance could grow on media containing 60 mM of glyphosate. The plasmid DNA, pGR1, was extracted and transformed back into E. coli JM109 by electroporation. As a control, the vector plasmid, pLA2917, was also transformed into JM109. The transformants were picked and tested on MOPS plates containing 20 mM glyphosate for glyphosate tolerance. The results showed that all pGR1 transformants have the ability to tolerate glyphosate, indicating that this ability resulted from transformation of pGR1.

5. Subcloning of High Glyphosate Tolerance DNA Fragment and Characterization of Glyphosate Tolerance Plasmid pGR1 DNA that showed highest tolerance to glyphosate was digested with different endonucleases: HindIII, PstI, HindIII+PstI, respectively. The inserted fragments were ligated with a vector plasmid DNA (pBlueScript KS or pGEM-3zf), and transformed into E. coli strain JM109. The transformants were selected on L-Broth media containing ampicillin by their colors (blue or white). The DNA of white colonies was extracted using the boiling method and screened for different recombinants. The recombinants were screened on MOPS media containing 20 mM glyphosate. Among the subclones, one glyphosate tolerant subclone, pGRH1, was chosen. The pGRH1 plasmid DNA was extracted and retransformed into JM109. The vector plasmid DNA was used as a control. The results showed that all pGRH1 transformants had the ability to tolerate glyphosate, indicating that this ability resulted from transformation of pGRH1. Based on the restriction enzyme digestion analysis of pGRH1 plasmid DNA, the full-length of the inserted fragment is 2.3 kb.

JM109 transformants containing pGR1, pGRH 1, and the control vector plasmid pGEM-3zf were inoculated at the same concentration (1%, based on the OD (absorbance density) values) into MOPS liquid media containing 50 mM and 150 mM glyphosate. The bacterial cultures were incubated at 37° C. for 24 hours with shaking. The ODs were measured at 600 nm. The results showed that JM109 recombinants containing pGR1 or pGRH1 could tolerate 150 mM glyphosate and grow normally, whereas JM109 recombinants containing the control vector plasmid could not.

Example 2

Sequence Analysis of High Glyphosate Tolerance Gene and Characterization of EPSP Synthase Functions 1. Sequence Analysis of High Glyphosate Tolerance Gene The full-length of the subcloned high glyphosate tolerance DNA fragment in Example 1 was sequenced. The sequencing results showed that this fragment, SEQ ID NO:1, is 1500 bp in length with an open reading frame of 1332 bp from bp 40 to 1371 (SEQ ID NO:3), encoding a predicated EPSP synthase of 444 amino acids (SEQ ID NO:2). A blast search showed that the subcloned high glyphosate tolerance DNA fragment shares no identity with other reported EPSP synthase genes (aroA) at the nucleotide level.

2. Characterization of EPSP Synthase Encoded by High Glyphosate Tolerance DNA Fragment DNA sequence analysis showed that high glyphosate tolerance subclone pGRH1 contains an open reading frame (ORF) for an EPSP synthase, In order to verify that the polypeptide encoded by this ORF exhibits glyphosate tolerance, the EPSP synthase mutant E. coli strain ER2799 was utilized as a receptor bacterium in a complementation assay. The high glyphosate tolerance subclone pGRH1 plasmid DNA was transformed into ER2799 using the $CaCl_2$ method. Transformants were picked up with sterile toothpicks and inoculated on MOPS media plates containing glyphosate. ER2799 and the vector plasmid (pBlueScript KS or pGEM-3zf) were used as negative controls. If the EPSP synthase encoded by pGRH1 complements the E. coli mutation, the transformants can grow by synthesizing amino acids from the inorganic substances in the restricted medium. Otherwise, the transformants cannot grow.

The complementation assay results revealed that DNA fragments in R3H1 and R7H1 transformed with pGRH1 could complement the E. coli EPSP synthase mutation. Hence, it was confirmed that the DNA fragment in subclone pGRH1 contains a fully functional EPSP synthase gene.

Example 3

Artificial Synthesis of High Glyphosate Tolerance EPSP Synthase Gene

Based on the sequence of the 1332 bp open reading frame in SEQ ID NO:1, the EPSP gene were divided into eight regions. Sixteen strands (positive and negative strands for each region) were designed and synthesized. These strands were 150-200 bp in length and had sequences for cohesive ends after annealing. The positive strands and their complementary negative strands were annealed to generate 8 double-stranded fragments with cohesive ends. All these fragments were mixed together and ligated into a full-length EPSP synthase gene with T4 ligase. This synthetic fragment contains 40-1374 bp of SEQ ID NO:1 and has XbaI and SacI recognition sites at the ends of the EPSP synthase gene.

This synthetic gene with XbaI and SacI recognition sites at its 5'- and 3'-ends was then used in construction of a plant expression vector containing the high glyphosate tolerance EPSP synthase gene.

Example 4

Construction of Plant Expression Vector Containing High Glyphosate Tolerance EPSP Synthase Gene The method used in construction of a plant expression vector containing a high glyphosate tolerance EPSP synthase gene was as follows:

A. The plant expression vector pBI121 (Clontech Co., Ltd) and pCAMBIA2301 (Clontech Co., Ltd) plasmid DNA was digested with two endonucleases HindIII and EcoRI. The fragment p35S-GUS-Nos-ter from the pBI121 plasmid DNA was ligated with pCAMBIA2301 plasmid DNA, resulting in an intermediate vector p35-2301-GUS.

B. Plasmid p35S-2301-GUS DNA was digested with two endonucleases XbaI and SacI, and ligated with the artificially synthesized EPSP synthase gene. A plant expression vector containing a high glyphosate tolerance EPSP synthase gene was thus obtained by replacing the GUS gene in the intermediate vector p35S-2301-GUS with the artificially synthesized EPSP synthase gene. The expression vector was then transformed into Agrobacterium tumefaciens EHA105, which was subsequently transferred into model plant tobacco to generate plants highly tolerant to glyphosate.

Example 5

Transformation of Tobacco to Generate Plants Highly Tolerant to Glyphosate Using Leaf Disc Protocol (1) A positive Agrobacterium tumefaciens EHA105 clone derived from Example 4 was picked up with a sterilized toothpick and inoculated into 2 ml YPE liquid containing kanamycin and streptomycin. The culture was incubated with shaking at 200 rpm and 28° C. for 24-36 hours.

(2) The culture was centrifuged at 4000 rpm for 15 minutes at room temperature.

(3) The upper aqueous layer was discarded and the pellet was resuspended in ½ MS solution, diluted to 5-20× of the original volume. $OD_{600}$ (absorbance density at 600 nm) was about 0.5.

(4) Transformation of tobacco was carried out according to the leaf disc transformation protocol, using sterilized tissue of a healthy leaf of about 2 weeks old. The main vein was removed and the leaf was cut into small pieces of 2 $cm^2$.

(5) The leaf discs were placed into prepared agrobacterial liquid for 2-5 minutes. The liquid was then drained off with sterile filters. The leaf discs were placed upside down on MS media plates and incubated in the dark at 28° C. for 48 hours.

(6) The discs were transferred, still upside down, to selection plates (MS+6-BA 1.0 mg/l+NAA 0.1 mg/l+Kan 50 mg/l+carbenicillin 250 mg/l). The plates were incubated at 25-28° C. under the light. After 7-15 days, callus formed.

(7) After about 20 days, shoots were cut from the callus when they were large enough to be distinguished from the stems. The shoots were placed into rooting media (½ MS+NAA 0.5 mg/l+Kanamycin 25 mg/l). Root formation occurred in 2-7 days.

(8) After development of the roots, plants were taken out. The attached solid culture media was washed off with sterile water. The plants were initially kept in a high humidity environment such as a plastic container with a glass cover for a few days. After the plants had grown stronger, the glass covers were removed, and the plants were transferred to solid culture media containing 10 mM glyphosate for screening of glyphosate tolerant plants.

(9) The glyphosate tolerant plants were reconfirmed by Southern, Northern and Western analyses.

(10) Glyphosate tolerance assays in greenhouse also confirmed that the transgenic plants could grow well in media containing 15 mM glyphosate.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims. All literatures cited herein are incorporated by reference in their entirety.

What is claimed is:

1. An isolated nucleic acid having
   (a) a nucleic acid sequence that encodes a polypeptide comprising an amino acid sequence that is at least 95% identical to SEQ ID NO:2, wherein the polypeptide, when present in a cell, increases the cell's ability to tolerate glyphosate, or
   (b) a nucleic acid sequence that is the full-length complement of the sequence of (a).

2. The isolated nucleic acid of claim 1, wherein the amino acid sequence is at least 99% identical to SEQ ID NO:2.

3. The isolated nucleic acid of claim 1, wherein the amino acid sequence is SEQ ID NO:2.

4. An isolated nucleic acid having
   (a) a nucleic acid sequence that encodes a polypeptide comprising the amino acid sequence of SEQ ID NO:2, or
   (b) a nucleic acid sequence that is the full-length complement of the sequence of (a).

5. An isolated nucleic acid having a nucleic acid sequence comprising SEQ ID NO: 1 or 3, or the full-length complement of SEQ ID NO: 1 or 3.

6. An isolated nucleic acid having a nucleic acid sequence consisting of SEQ ID NO:1 or 3, or the full-length complement of SEQ ID NO: 1 or 3.

7. A vector comprising the nucleic acid of claim 1 operably linked to an expression control sequence.

8. A vector comprising the nucleic acid of claim 2 operably linked to an expression control sequence.

9. A vector comprising the nucleic acid of claim 3 operably linked to an expression control sequence.

10. A vector comprising the nucleic acid of claim 4 operably linked to an expression control sequence.

11. A vector comprising the nucleic acid of claim 5 operably linked to an expression control sequence.

12. A cultured cell comprising the nucleic acid of claim 1 operably linked to an expression control sequence.

13. A cultured cell comprising the nucleic acid of claim 2 operably linked to an expression control sequence.

14. A cultured cell comprising the nucleic acid of claim 3 operably linked to an expression control sequence.

15. A cultured cell comprising the nucleic acid of claim 4 operably linked to an expression control sequence.

16. A cultured cell comprising the nucleic acid of claim 5 operably linked to an expression control sequence.

17. A transgenic plant comprising the nucleic acid of claim 1 operably linked to an expression control sequence.

18. The transgenic plant of claim 17, wherein the plant is soybean, cotton, alfalfa, canola, flax, tomato, sugar beet, sunflower, potato, tobacco, corn, wheat, rice, lettuce or rape.

19. A transgenic tobacco or rape comprising the nucleic acid of claim 1 operably linked to an expression control sequence.

20. A transgenic plant comprising the nucleic acid of claim 2 operably linked to an expression control sequence.

21. The transgenic plant of claim 20, wherein the plant is soybean, cotton, alfalfa, canola, flax, tomato, sugar beet, sunflower, potato, tobacco, corn, wheat, rice, lettuce or rape.

22. A transgenic tobacco or rape comprising the nucleic acid of claim 2 operably linked to an expression control sequence.

23. A transgenic plant comprising the nucleic acid of claim 3 operably linked to an expression control sequence.

24. The transgenic plant of claim 23, wherein the plant is soybean, cotton, alfalfa, canola, flax, tomato, sugar beet, sunflower, potato, tobacco, corn, wheat, rice, lettuce or rape.

25. A transgenic tobacco or rape comprising the nucleic acid of claim 3 operably linked to an expression control sequence.

26. A transgenic plant comprising the nucleic acid of claim 4 operably linked to an expression control sequence.

27. The transgenic plant of claim 26, wherein the plant is soybean, cotton, alfalfa, canola, flax, tomato, sugar beet, sunflower, potato, tobacco, corn, wheat, rice, lettuce or rape.

28. A transgenic tobacco or rape comprising the nucleic acid of claim 4 operably linked to an expression control sequence.

29. A transgenic plant comprising the nucleic acid of claim 5 operably linked to an expression control sequence.

30. The transgenic plant of claim 29, wherein the plant is soybean, cotton, alfalfa, canola, flax, tomato, sugar beet, sunflower, potato, tobacco, corn, wheat, rice lettuce or rape.

31. A transgenic tobacco or rape comprising the nucleic acid of claim 5 operably linked to an expression control sequence.

32. A method of increasing a plant's ability to tolerate glyphosate, comprising:
    introducing the vector of claim 7 into a plant cell;
    cultivating the plant cell; and
    regenerating a transgenic plant from the cell, wherein the transgenic plant has increased tolerance to glyphosate.

33. A method of increasing a plant's ability to tolerate glyphosate, comprising:
    introducing the vector of claim 8 into a plant cell;
    cultivating the plant cell; and
    regenerating a transgenic plant from the cell, wherein the transgenic plant has increased tolerance to glyphosate.

34. A method of increasing a plant's ability to tolerate glyphosate, comprising:
    introducing the vector of claim 9 into a plant cell;
    cultivating the plant cell; and
    regenerating a transgenic plant from the cell, wherein the transgenic plant has increased tolerance to glyphosate.

35. A method of increasing a plant's ability to tolerate glyphosate, comprising:
    introducing the vector of claim 10 into a plant cell;
    cultivating the plant cell; and
    regenerating a transgenic plant from the cell, wherein the transgenic plant has increased tolerance to glyphosate.

36. A method of increasing a plant's ability to tolerate glyphosate, comprising:
    introducing the vector of claim 11 into a plant cell;
    cultivating the plant cell; and
    regenerating a transgenic plant from the cell, wherein the transgenic plant has increased tolerance to glyphosate.

* * * * *

SEQUENCE LISTING

```
<160> NUMBER OF SEQ ID NOS: 41

<210> SEQ ID NO 1
<211> LENGTH: 1500
<212> TYPE: DNA
<213> ORGANISM: Unknown
<220> FEATURE:
<223> OTHER INFORMATION: Unknown bacterium

<400> SEQUENCE: 1
ctcctacagt tagggcaagt cccccaccac tcgacaagca tggcgtgttt gcctgatgat      60
tcgggtccgc atgtcggcca ctccacgcca cctcgccttg accaggagcc ttgtaccttg     120
agttcgcaga aaaccgtgac cgttacaccg cccaacttcc ccctcactgg caaggtcgcg     180
```

```
cccccccggct ccaaatccat taccaaccgt gcgctgttgc tggcggcatt ggccaagggc    240
accagccgtt tgagcggtgc gctcaaaagc gatgacacgc ccacatgtc ggtcgccctg    300 cggcagatgg cgtcaccat cgacgagccg gacgacacca cctttgtggt caccagccaa    360
ggctcgctgc aattgccggc ccagccgttg ttcctcggca acgctggcac cgccatgcgc    420
tttctcacgg ctgccgtggc caccgtgcaa ggcaccgtgg tactggacgg cgacgagtac    480
atgcaaaaac gcccgattgg cccgctgctg gctaccctgg ccagaacgg catccaggtc    540 gacagcccca ccggttgccc accggtcacc gtgcacggca tgggcaaggt ccaggccaag    600
cgtttcgaga ttgatggtgg tttgtccagc cagtacgtat cggccctgct gatgctcgcg    660
gcgtgcggcg aagcgccgat tgaagtggcg ctgaccggca aggatatcgg tgcccgtggc    720
tacgtggacc tgaccctcga ctgcatgcgt gccttcgggg cccaggtgga cgccgtggac    780
gacaccacct ggcgcgtcgc ccccaccggc tataccgccc atgattacct gatcgaaccc    840
gatgcgtccg ccgccacgta tttgtgggcc gcagaagtgc tgaccggtgg gcgtatcgac    900
atcggcgtag ccgcgcagga cttcacccag cccgacgcca aggcccaggc cgtgattgcg    960
cagttcccga acatgcaagc cacggtggta ggctcgcaaa tgcaggatgc gatcccgacc   1020
ctggcggtgc tcgccgcgtt caacaacacc ccggtgcgtt tcactgaact ggcgaacctg   1080
cgcgtcaagg aatgtgaccg cgtgcaggcg ctgcacgatg gcctcaacga aattcgcccg   1140
ggcctggcga ccatcgaggg cgatgacctg ctggtcgcca gcgacccggc cctggcaggc   1200
accgcctgca ccgcactgat cgacacccac gccgaccatc gcatcgccat gtgctttgcc   1260
ctggccgggc ttaaagtctc gggcattcgc attcaagacc cggactgcgt ggccaagacc   1320
taccctgact actggaaagc ctggcccagc ctgggcgttc acctaaacga ctgacacaca   1380
aaacctgtag cagagcttgc tcgcgaaaaa cgcacacgtg ccgcgtttgt tcaggaaaca   1440
cgcgttatcg ttgacgttta tcgagctaag ctcgctccta cattttgcag cgagatcttg   1500
```

<210> SEQ ID NO 2
<211> LENGTH: 444
<212> TYPE: PRT
<213> ORGANISM: Unknown
<220> FEATURE:
<223> OTHER INFORMATION: Unknown bacterium

<400> SEQUENCE: 2

```
Met Ala Cys Leu Pro Asp Asp Ser Gly Pro His Val Gly His Ser Thr
1               5                   10                  15

Pro Pro Arg Leu Asp Gln Glu Pro Cys Thr Leu Ser Ser Gln Lys Thr
            20                  25                  30

Val Thr Val Thr Pro Pro Asn Phe Pro Leu Thr Gly Lys Val Ala Pro
        35                  40                  45

Pro Gly Ser Lys Ser Ile Thr Asn Arg Ala Leu Leu Ala Ala Leu
    50                  55                  60

Ala Lys Gly Thr Ser Arg Leu Ser Gly Ala Leu Lys Ser Asp Asp Thr
65                  70                  75                  80

Arg His Met Ser Val Ala Leu Arg Gln Met Gly Val Thr Ile Asp Glu
                85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
```

```
                130             135             140
Asp Glu Tyr Met Gln Lys Arg Pro Ile Gly Pro Leu Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Met Gly Lys Val Gln Ala Lys Arg Phe Glu Ile Asp
            180                 185                 190

Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
    210                 215                 220

Ala Arg Gly Tyr Val Asp Leu Thr Leu Asp Cys Met Arg Ala Phe Gly
225                 230                 235                 240

Ala Gln Val Asp Ala Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
    290                 295                 300

Val Ile Ala Gln Phe Pro Asn Met Gln Ala Thr Val Val Gly Ser Gln
305                 310                 315                 320

Met Gln Asp Ala Ile Pro Thr Leu Ala Val Leu Ala Ala Phe Asn Asn
                325                 330                 335

Thr Pro Val Arg Phe Thr Glu Leu Ala Asn Leu Arg Val Lys Glu Cys
            340                 345                 350

Asp Arg Val Gln Ala Leu His Asp Gly Leu Asn Glu Ile Arg Pro Gly
        355                 360                 365

Leu Ala Thr Ile Glu Gly Asp Asp Leu Leu Val Ala Ser Asp Pro Ala
    370                 375                 380

Leu Ala Gly Thr Ala Cys Thr Ala Leu Ile Asp Thr His Ala Asp His
385                 390                 395                 400

Arg Ile Ala Met Cys Phe Ala Leu Ala Gly Leu Lys Val Ser Gly Ile
                405                 410                 415

Arg Ile Gln Asp Pro Asp Cys Val Ala Lys Thr Tyr Pro Asp Tyr Trp
            420                 425                 430

Lys Ala Trp Pro Ser Leu Gly Val His Leu Asn Asp
        435                 440

<210> SEQ ID NO 3
<211> LENGTH: 1332
<212> TYPE: DNA
<213> ORGANISM: Unknown
<220> FEATURE:
<223> OTHER INFORMATION: Unknown bacterium

<400> SEQUENCE: 3
atggcgtgtt tgcctgatga ttcgggtccg catgtcggcc actccacgcc acctcgcctt    60
gaccaggagc cttgtacctt gagttcgcag aaaaccgtga ccgttacacc gcccaacttc   120
cccctcactg gcaaggtcgc gccccccggc tccaaatcca ttaccaaccg tgcgctgttg   180
ctggcggcat tggccaaggg caccagccgt tgagcggtg cgctcaaaag cgatgacacg   240
cgccacatgt cggtcgccct gcggcagatg ggcgtcacca tcgacgagcc ggacgacacc   300
```

-continued

```
accctttgtgg tcaccagcca aggctcgctg caattgccgg cccagccgtt gttcctcggc    360
aacgctggca ccgccatgcg ctttctcacg gctgccgtgg ccaccgtgca aggcaccgtg    420
gtactggacg gcgacgagta catgcaaaaa cgcccgattg gccgctgct ggctaccctg     480 ggccagaacg gcatccaggt cgacagcccc accggttgcc caccggtcac cgtgcacggc    540
atgggcaagg tccaggccaa gcgtttcgag attgatggtg gtttgtccag ccagtacgta    600
tcggccctgc tgatgctcgc ggcgtgcggc gaagcgccga ttgaagtggc gctgaccggc    660
aaggatatcg gtgcccgtgg ctacgtggac ctgaccctcg actgcatgcg tgccttcggg    720
gcccaggtgg acgccgtgga cgacaccacc tggcgcgtcg cccccaccgg ctataccgcc    780
catgattacc tgatcgaacc cgatgcgtcc gccgccacgt atttgtgggc cgcagaagtg    840
ctgaccggtg ggcgtatcga catcggcgta gccgcgcagg acttcaccca gcccgacgcc    900
aaggcccagg ccgtgattgc gcagttcccg aacatgcaag ccacggtggt aggctcgcaa    960
atgcaggatg cgatcccgac cctggcggtg ctcgccgcgt tcaacaacac cccggtgcgt   1020
ttcactgaac tggcgaacct gcgcgtcaag gaatgtgacc gcgtgcaggc gctgcacgat   1080
ggcctcaacg aaattcgccc gggcctggcg accatcgagg gcgatgacct gctggtcgcc   1140
agcgacccgg ccctggcagg caccgcctgc accgcactga tcgacaccca cgccgaccat   1200
cgcatcgcca tgtgctttgc cctggccggg cttaaagtct cgggcattcg cattcaagac   1260
ccggactgcg tggccaagac ctaccctgac tactggaaag cctggcccag cctgggcgtt   1320
cacctaaacg ac                                                        1332
```

<210> SEQ ID NO 4
<211> LENGTH: 7
<212> TYPE: PRT
<213> ORGANISM: Petunia
<300> PUBLICATION INFORMATION:
<310> PATENT DOCUMENT NUMBER: US 5,310,667
<312> PUBLICATION DATE: 1994-05-10

<400> SEQUENCE: 4

Leu Gly Asn Ala Ala Thr Ala
1               5

<210> SEQ ID NO 5
<211> LENGTH: 9
<212> TYPE: PRT
<213> ORGANISM: Petunia
<220> FEATURE:
<221> NAME/KEY: VARIANT
<222> LOCATION: (5)..(5)
<223> OTHER INFORMATION: Alanine, serine or threonine
<300> PUBLICATION INFORMATION:
<310> PATENT DOCUMENT NUMBER: US 5,310,667
<312> PUBLICATION DATE: 1994-05-10

<400> SEQUENCE: 5

Ala Leu Leu Met Xaa Ala Pro Leu Thr
1               5

<210> SEQ ID NO 6
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (5)..(6)
<223> OTHER INFORMATION: Any amino acid -continued

```
<220> FEATURE:
<221> NAME/KEY: VARIANT
<222> LOCATION: (9)..(10)
<223> OTHER INFORMATION: Any amino acid
<220> FEATURE:
<221> NAME/KEY: VARIANT
<222> LOCATION: (11)..(11)
<223> OTHER INFORMATION: Arginine or lysine
<220> FEATURE:
<221> NAME/KEY: VARIANT
<222> LOCATION: (12)..(13)
<223> OTHER INFORMATION: Any amino acid
<220> FEATURE:
<221> NAME/KEY: VARIANT
<222> LOCATION: (14)..(14)
<223> OTHER INFORMATION: Aspartic acid or asparagine
<300> PUBLICATION INFORMATION:
<310> PATENT DOCUMENT NUMBER: US 5,633,435
<312> PUBLICATION DATE: 1997-05-27

<400> SEQUENCE: 6

Glu Arg Pro Ile Xaa Xaa Leu Val Xaa Xaa Xaa Xaa Xaa Xaa Ala
1               5                   10                  15

<210> SEQ ID NO 7
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: Glycine, serine, threonine, cysteine, tyrosine,
      asparagine, glutamine, aspartic acid, or glutamic acid
<220> FEATURE:
<221> NAME/KEY: VARIANT
<222> LOCATION: (4)..(4)
<223> OTHER INFORMATION: Serine or threonine
<300> PUBLICATION INFORMATION:
<310> PATENT DOCUMENT NUMBER: US 5,633,435
<312> PUBLICATION DATE: 1997-05-27

<400> SEQUENCE: 7

Arg Xaa His Xaa Glu
1               5

<210> SEQ ID NO 8
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (4)..(4)
<223> OTHER INFORMATION: Serine or threonine
<300> PUBLICATION INFORMATION:
<310> PATENT DOCUMENT NUMBER: US 5,633,435
<312> PUBLICATION DATE: 1997-05-27

<400> SEQUENCE: 8

Gly Asp Lys Xaa
1

<210> SEQ ID NO 9
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
```

```
<222> LOCATION: (4)..(4)
<223> OTHER INFORMATION: Alanine, arginine, asparagine, aspartic acid,
      cysteine, glutamine, glutamic acid, glycine, histidine,
      isoleucine, leucine, lysine, methionine, phenylalanine, proline,
      serine, threonine, tryptophan, tyrosine, or valine
<300> PUBLICATION INFORMATION:
<310> PATENT DOCUMENT NUMBER: US 5,633,435
<312> PUBLICATION DATE: 1997-05-27

<400> SEQUENCE: 9

Ser Ala Gln Xaa Lys
1               5

<210> SEQ ID NO 10
<211> LENGTH: 4
<212> TYPE: PRT
<213> ORGANISM: Petunia
<220> FEATURE:
<221> NAME/KEY: VARIANT
<222> LOCATION: (2)..(2)
<223> OTHER INFORMATION: Alanine, arginine, asparagine, aspartic acid,
      cysteine, glutamine, glutamic acid, glycine, histidine,
      isoleucine, leucine, lysine, methionine, phenylalanine, proline,
      serine, threonine, tryptophan, tyrosine, or valine
<300> PUBLICATION INFORMATION:
<310> PATENT DOCUMENT NUMBER: US 5,866,775
<312> PUBLICATION DATE: 1999-02-02

<400> SEQUENCE: 10

Asn Xaa Thr Arg
1

<210> SEQ ID NO 11
<211> LENGTH: 9
<212> TYPE: PRT
<213> ORGANISM: Unknown
<220> FEATURE:
<223> OTHER INFORMATION: Unknown bacterium
<220> FEATURE:
<221> NAME/KEY: VARIANT
<222> LOCATION: (5)..(5)
<223> OTHER INFORMATION: Alanine, serine, or threonine

<400> SEQUENCE: 11

Ala Leu Leu Met Xaa Ala Pro Leu Thr
1               5

<210> SEQ ID NO 12
<211> LENGTH: 32
<212> TYPE: PRT
<213> ORGANISM: Unknown
<220> FEATURE:
<223> OTHER INFORMATION: Unknown bacterium

<400> SEQUENCE: 12

Gly Lys Val Ala Pro Pro Gly Ser Lys Ser Ile Thr Asn Arg Ala Leu
1               5                   10                  15

Leu Leu Ala Ala Leu Ala Lys Gly Thr Ser Arg Leu Ser Gly Ala Leu
            20                  25                  30

<210> SEQ ID NO 13
<211> LENGTH: 19
<212> TYPE: PRT
<213> ORGANISM: Unknown
<220> FEATURE:
<223> OTHER INFORMATION: Unknown bacterium

<400> SEQUENCE: 13

Leu Phe Leu Gly Asn Ala Gly Thr Ala Met Arg Phe Leu Thr Ala Ala
```

```
1               5                   10                  15
Val Ala Thr

<210> SEQ ID NO 14
<211> LENGTH: 27
<212> TYPE: PRT
<213> ORGANISM: Unknown
<220> FEATURE:
<223> OTHER INFORMATION: Unknown bacterium

<400> SEQUENCE: 14

Val Leu Asp Gly Asp Glu Tyr Met Gln Lys Arg Pro Ile Gly Pro Leu
1               5                   10                  15

Leu Ala Thr Leu Gly Gln Asn Gly Ile Gln Val
            20                  25

<210> SEQ ID NO 15
<211> LENGTH: 51
<212> TYPE: PRT
<213> ORGANISM: Unknown
<220> FEATURE:
<223> OTHER INFORMATION: Unknown bacterium

<400> SEQUENCE: 15

Leu Ala Val Leu Ala Ala Phe Asn Asn Thr Pro Val Arg Phe Thr Glu
1               5                   10                  15

Leu Ala Asn Leu Arg Val Lys Glu Cys Asp Arg Val Gln Ala Leu His
            20                  25                  30

Asp Gly Leu Asn Glu Ile Arg Pro Gly Leu Ala Thr Ile Glu Gly Asp
        35                  40                  45

Asp Leu Leu
    50

<210> SEQ ID NO 16
<211> LENGTH: 18
<212> TYPE: PRT
<213> ORGANISM: Unknown
<220> FEATURE:
<223> OTHER INFORMATION: Unknown bacterium

<400> SEQUENCE: 16

Ile Asp Thr His Ala Asp His Arg Ile Ala Met Cys Phe Ala Leu Ala
1               5                   10                  15

Gly Leu

<210> SEQ ID NO 17
<211> LENGTH: 18
<212> TYPE: PRT
<213> ORGANISM: Unknown
<220> FEATURE:
<223> OTHER INFORMATION: Unknown bacterium

<400> SEQUENCE: 17

Leu Thr Gly Lys Asp Ile Gly Ala Arg Gly Tyr Val Asp Leu Thr Leu
1               5                   10                  15

Asp Cys

<210> SEQ ID NO 18
<211> LENGTH: 23
<212> TYPE: PRT
<213> ORGANISM: Escherichia coli

<400> SEQUENCE: 18
```

```
Asp Ile Val Leu Thr Gly Glu Pro Arg Met Lys Glu Arg Pro Ile Gly
1               5                   10                  15

His Leu Val Asp Ala Leu Arg
            20
```

<210> SEQ ID NO 19
<211> LENGTH: 23
<212> TYPE: PRT
<213> ORGANISM: Unknown
<220> FEATURE:
<223> OTHER INFORMATION: Unknown bacterium

<400> SEQUENCE: 19

```
Thr Val Val Leu Asp Gly Asp Glu Tyr Met Gln Lys Arg Pro Ile Gly
1               5                   10                  15

Pro Leu Leu Ala Thr Leu Gly
            20
```

<210> SEQ ID NO 20
<211> LENGTH: 23
<212> TYPE: PRT
<213> ORGANISM: Petunia

<400> SEQUENCE: 20

```
Arg Tyr Val Leu Asp Gly Val Pro Arg Met Arg Glu Arg Pro Ile Ser
1               5                   10                  15

Asp Leu Val Asp Gly Leu Lys
            20
```

<210> SEQ ID NO 21
<211> LENGTH: 21
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (15)..(15)
<223> OTHER INFORMATION: Any amino acid

<400> SEQUENCE: 21

```
Ile Val Leu Asp Gly Pro Arg Met Lys Glu Arg Pro Ile Gly Xaa Leu
1               5                   10                  15

Val Asp Ala Leu Lys
            20
```

<210> SEQ ID NO 22
<211> LENGTH: 16
<212> TYPE: PRT
<213> ORGANISM: Escherichia coli

<400> SEQUENCE: 22

```
Asp Val Asp Gly Ser Val Ser Ser Gln Phe Leu Thr Ala Leu Leu Met
1               5                   10                  15
```

<210> SEQ ID NO 23
<211> LENGTH: 16
<212> TYPE: PRT
<213> ORGANISM: Unknown
<220> FEATURE:
<223> OTHER INFORMATION: Unknown bacterium

<400> SEQUENCE: 23

```
Glu Ile Asp Gly Gly Leu Ser Ser Gln Tyr Val Ser Ala Leu Leu Met
```

-continued

<210> SEQ ID NO 24
<211> LENGTH: 16
<212> TYPE: PRT
<213> ORGANISM: Petunia

<400> SEQUENCE: 24

Lys Leu Ser Gly Ser Ile Ser Ser Gln Tyr Leu Thr Ala Leu Leu Met
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Consensus sequence

<400> SEQUENCE: 25

Asp Ile Asp Gly Ser Ile Ser Ser Gln Tyr Leu Thr Ala Leu Leu Met
1               5                   10                  15

<210> SEQ ID NO 26
<211> LENGTH: 14
<212> TYPE: PRT
<213> ORGANISM: Escherichia coli

<400> SEQUENCE: 26

Asn His Ile Pro Asp Ala Ala Met Thr Ile Ala Thr Ala Ala
1               5                   10

<210> SEQ ID NO 27
<211> LENGTH: 13
<212> TYPE: PRT
<213> ORGANISM: Unknown
<220> FEATURE:
<223> OTHER INFORMATION: Unknown bacterium

<400> SEQUENCE: 27

Gln Met Gln Asp Ala Ile Pro Thr Leu Ala Val Leu Ala
1               5                   10

<210> SEQ ID NO 28
<211> LENGTH: 14
<212> TYPE: PRT
<213> ORGANISM: Petunia

<400> SEQUENCE: 28

Asn Lys Met Pro Asp Val Ala Met Thr Leu Ala Val Val Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: Any amino acid

<400> SEQUENCE: 29

Asn Xaa Met Pro Asp Ala Ala Met Thr Leu Ala Val Leu Ala
1               5                   10

```
<210> SEQ ID NO 30
<211> LENGTH: 15
<212> TYPE: PRT
<213> ORGANISM: Escherichia coli

<400> SEQUENCE: 30

Ile Tyr Asn Trp Arg Val Lys Glu Thr Asp Arg Leu Phe Ala Met
1               5                   10                  15

<210> SEQ ID NO 31
<211> LENGTH: 15
<212> TYPE: PRT
<213> ORGANISM: Unknown
<220> FEATURE:
<223> OTHER INFORMATION: Unknown bacterium

<400> SEQUENCE: 31

Leu Ala Asn Leu Arg Val Lys Glu Cys Asp Arg Val Gln Ala Leu
1               5                   10                  15

<210> SEQ ID NO 32
<211> LENGTH: 17
<212> TYPE: PRT
<213> ORGANISM: Petunia

<400> SEQUENCE: 32

Val Ala Ser Trp Arg Val Lys Glu Thr Glu Arg Glu Arg Met Ile Ala
1               5                   10                  15

Ile

<210> SEQ ID NO 33
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (13)..(13)
<223> OTHER INFORMATION: Any amino acid

<400> SEQUENCE: 33

Ile Ala Asn Trp Arg Val Lys Glu Thr Asp Arg Leu Xaa Ala Ile
1               5                   10                  15

<210> SEQ ID NO 34
<211> LENGTH: 13
<212> TYPE: PRT
<213> ORGANISM: Escherichia coli

<400> SEQUENCE: 34

Thr Tyr Asn Asp His Arg Met Ala Met Cys Phe Ser Leu
1               5                   10

<210> SEQ ID NO 35
<211> LENGTH: 13
<212> TYPE: PRT
<213> ORGANISM: Unknown
<220> FEATURE:
<223> OTHER INFORMATION: Unknown bacterium

<400> SEQUENCE: 35

Thr His Ala Asp His Arg Ile Ala Met Cys Phe Ala Leu
1               5                   10

<210> SEQ ID NO 36
```

-continued

```
<211> LENGTH: 13
<212> TYPE: PRT
<213> ORGANISM: Petunia

<400> SEQUENCE: 36

Thr Tyr Asp Asp His Arg Met Ala Met Ala Phe Ser Leu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (3)..(3)
<223> OTHER INFORMATION: Any amino acid

<400> SEQUENCE: 37

Thr Tyr Xaa Asp His Arg Met Ala Met Cys Phe Ser Leu
1               5                   10

<210> SEQ ID NO 38
<211> LENGTH: 12
<212> TYPE: PRT
<213> ORGANISM: Escherichia coli

<400> SEQUENCE: 38

Lys Cys Thr Ala Lys Thr Phe Pro Asp Tyr Phe Glu
1               5                   10

<210> SEQ ID NO 39
<211> LENGTH: 12
<212> TYPE: PRT
<213> ORGANISM: Unknown
<220> FEATURE:
<223> OTHER INFORMATION: Unknown bacterium

<400> SEQUENCE: 39

Asp Cys Val Ala Lys Thr Tyr Pro Asp Tyr Trp Lys
1               5                   10

<210> SEQ ID NO 40
<211> LENGTH: 12
<212> TYPE: PRT
<213> ORGANISM: Petunia

<400> SEQUENCE: 40

Gly Cys Thr Arg Lys Thr Phe Pro Asn Tyr Phe Asp
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Consensus sequence

<400> SEQUENCE: 41

Cys Thr Ala Lys Thr Phe Pro Asp Tyr Phe Asp
1               5                   10
```